(12) United States Patent
You

(10) Patent No.: US 9,532,925 B2
(45) Date of Patent: Jan. 3, 2017

(54) SPECTRAL ELECTROTHERAPY DEVICE AND METHOD OF CONTROLLING THE SAME

(71) Applicant: HYPER SPECTRUM CORPORATION, Taipei (TW)

(72) Inventor: Link You, Taoyuan County (TW)

(73) Assignee: HYPER SPECTRUM CORPORATION, Taipei (TW)

( * ) Notice: Subject to any disclaimer, the term of this patent is extended or adjusted under 35 U.S.C. 154(b) by 135 days.

(21) Appl. No.: 14/573,879

(22) Filed: Dec. 17, 2014

(65) Prior Publication Data
US 2016/0175191 A1    Jun. 23, 2016

(51) Int. Cl.
*A61N 1/00* (2006.01)
*A61H 39/00* (2006.01)
(52) U.S. Cl.
CPC ..... *A61H 39/002* (2013.01); *A61H 2201/5005* (2013.01)

(58) Field of Classification Search
CPC .. A61N 1/32; A61N 1/36021; A61N 1/36071; A61H 39/002
USPC .......................................................... 607/76
See application file for complete search history.

*Primary Examiner* — Amanda Patton
*Assistant Examiner* — Philip C Edwards
(74) *Attorney, Agent, or Firm* — WPAT, P.C., Intellectual Property Attorneys; Anthony King

(57) ABSTRACT

A spectral electrotherapy device and a method of controlling the same are introduced, wherein a central processing unit provides a control signal for controlling the switching operation of an output driver to generate output voltage, thereby controlling output features of the spectral electrotherapy device. The control signal provided by the central processing unit to a switching unit uses central frequency $f_0$ as a standard to thereby define the bandwidth of the central frequency $f_0$ with difference $\Delta f$ and define the points in time of the next change in the central frequency $f_0$ and the difference $\Delta f$ with first and second time intervals t1, t2, respectively. Values of the central frequency $f_0$, the difference $\Delta f$, the first time interval t1, the second time interval t2 are generated from a dynamic parameter generating unit in different points in time. Electrical stimulation thus performed on the human body is complete and comprehensive.

12 Claims, 7 Drawing Sheets

SPECTRAL ELECTROTHERAPY DEVICE AND METHOD OF CONTROLLING THE SAME

FIELD OF THE INVENTION

The present invention relates to electrotherapy devices and methods of controlling the same, and more particularly, to a spectral electrotherapy device and a method of controlling the same.

BACKGROUND OF THE INVENTION

Conventional Chinese medical treatments, such as acupuncture and tuina, which achieve efficacy by stimulating acupuncture points of the human body, improve as a result of technological advancement, thereby developing electrotherapy devices which stimulate acupuncture points of the human body by an output voltage to therefore achieve a known level of efficacy and provide users with an alternative to conventional Chinese medical treatments.

Electrotherapy devices come in three types: low-frequency (below 1 kHz) electrotherapy devices, medium-frequency (1 kHz~100kHz) electrotherapy devices, and high-frequency (above 100 kHz) electrotherapy devices. Low-frequency and medium-frequency electrotherapy devices are commercially available. For instance, low-frequency electrotherapy devices operate by Transcutaneous Electrical Nerve Stimulation (TENS) and Electrical Muscle Stimulation (EMS), whereas medium-frequency electrotherapy devices work with a vector interference electrotherapy apparatus and a medium-frequency modulated electrotherapy device.

Electrotherapy effectuates stimulation of the human body's nerves, muscles, and cells with appropriate electrical signals (which depend on parameters, such as voltage level, frequency, duty cycle, and stimulation duration.) Electrotherapy is a therapeutic technique derived from an acupuncture theory based on a combination of rehabilitation medical engineering and traditional Chinese medicine. According to traditional Chinese medicine and rehabilitation theory, acupuncture points lie beneath the skin of the human body and have a specific depth and scope.

Electrotherapy devices pass output signals to the human body through the human skin. From the perspective of electricity, impedance features of the human skin originate in "capacitive impedance." Hence, equivalent features of the human skin are quite similar to that of a "capacitor," and therefore they can be described with the following mathematical equations: $Xc=1/\omega c$, $\omega=2\pi f$, where f denotes frequency, and Xc denotes capacitive impedance, wherein frequency is inversely proportional to capacitive impedance. Therefore, the higher the frequency of an output signal of an electrotherapy device, the lower the impedance of the human skin, such that the output signal can reach the human body's tissues. Conversely, the lower the frequency of the output signal of the electrotherapy device, the higher the impedance of the human skin, such that the output signal acts on the surface of the skin rather than goes deep into the human body's tissues.

Therefore, the effective depth of electrotherapy devices depends on the frequency of the output signal. During their electrotherapy session, conventional electrotherapy devices always make their carrier waves operate at a fixed frequency. For "a plurality of" outputs of vector interference electrotherapy devices to produce interference effect (for preventing the human body's self-adaptation to an output voltage with a fixed frequency), it is necessary that the frequencies of its two outputs approximate to each other. Therefore, from the perspective of effective depth analysis, the electrotherapy effect results from a change in a small range of frequencies. After use for a while, although it postpones the human body's self-adaptation to the output voltage, the human body's self-adaptation will occur anyway.

Therefore, conventional electrotherapy devices are subject to limits because of the design of carrier wave frequency. As a result, during their electrotherapy session, they are confined to a specific effective depth (the depth below the skin) and therefore are not changeable, and in consequence areas other than the acting area cannot be fully stimulated. For instance, since their carrier wave frequency is fixed, conventional electrotherapy devices are subject to limits in both effective depth and scope. As a result, in the course of electrotherapy, stimulation is restricted to trigger points or acupuncture points of a specific depth, and in consequence stimulation cannot fully affect trigger points or acupuncture points which are nearby and have different depths. In another aspect, since electrotherapy produces stimulation effect by an output voltage with a frequency, as described above, from the perspective of the human body, after identical frequencies or similar frequencies have persisted for a period of time, the human body undergoes self-adaptation and thereby adapts to the frequency, and in consequence the stimulation effect of electrotherapy dwindles greatly. To circumvent the human body's adaptation to a fixed pulse frequency, vector interference electrotherapy devices adopt mutual interference of two frequencies to block the self-adaptation mechanism of the human body. However, vector interference electrotherapy devices are still confronted with problems, for example, the human body's adaptation to the effective depth, acting scope, and long use, as well as drawbacks, for example, the two outputs cause the electrotherapy devices to incur high manufacturing costs and require high power consumption.

Moreover, conventional electrotherapy devices have further drawbacks. For instance, in the course of generating an output voltage, the switching speed is so low that the waveform of the pulse generated is inconspicuous, thereby compromising the effect of electrical stimulation. In addition, conventional electrotherapy devices control pulse strength (voltage level) by the adjustment performed with a built-in variable resistor of the switching unit, and in consequence it is difficult for electrotherapy devices to perform adjustment for the sake of fine variations, thereby rendering it difficult for users to perform adjustment in order to attain an appropriate electrical stimulation level (i.e., voltage level). Furthermore, the switching unit of conventional electrotherapy devices is likely to generate residual heat and therefore the operating temperature of the electrotherapy devices is usually high. Therefore, it is important to overcome the aforesaid drawbacks of the conventional electrotherapy devices.

SUMMARY OF THE INVENTION

It is an objective of the present invention to generate a continuous and ever-changing voltage signal by a spectrum rather than a conventional pulse signal of a single frequency, so as to solve known problems, including the human body's self-adaptation to a signal frequency and failure to expand the effective depth and scope.

In order to achieve the above and other objectives, the present invention provides a spectral electrotherapy device, having a central processing unit for providing a control signal to a switching unit of an output driver such that a voltage source provided by a power supply connected to the output driver generates an output voltage through a switching operation performed by the output driver, wherein the output voltage is sent to an electrode assembly connected to the output driver to thereby generate an output of the spectral electrotherapy device, characterized in that: the central processing unit uses a central frequency $f_0$ as a standard for the control signal provided by the corresponding switching unit to define a bandwidth of the central frequency $f_0$ with a difference $\Delta f$, define a point in time of a next change in the central frequency $f_0$ with first time interval t1, and define a point in time of a next change in the difference $\Delta f$ with second time interval t2, wherein values of the central frequency $f_0$, the difference $\Delta f$, the first time interval t1, and the second time interval t2 change continuously while the output driver is operating so as for the central processing unit to generate the control signal in accordance with the operation of a dynamic parameter generating unit. Therefore, the present invention effectuates plenty of carrier wave changes in a short period of time through the computation capability of a conventional central processing unit, for example, outputting carrier waves of tens of thousands of different frequencies in 1~2 seconds.

In an embodiment of the present invention, the control signal defined jointly with the central frequency $f_0$ and the difference $\Delta f$ is controlled by the central processing unit to oscillate at 1k~100 kHz. Therefore, the area subjected to electrical stimulation extends from the point of contact between the electrode assembly and the skin to the inner layers of the human body's tissues to therefore form a wide area subjected to repetitious electrical stimulation, such that acupuncture points, lesions, or trigger points lying at different depths in the human body's tissues can be stimulated completely and comprehensively.

In order to achieve the above and other objectives, the present invention provides a method of controlling a spectral electrotherapy device, wherein the spectral electrotherapy device provides a control signal to a switching unit of an output driver through a central processing unit, such that a voltage source provided by a power supply connected to the output driver generates an output voltage through the switching operation of the output driver, wherein the output voltage is sent to an electrode assembly connected to the output driver for generating an output of the spectral electrotherapy device, the method is characterized in that: the control signal uses a central frequency $f_0$ as the standard to thereby define the bandwidth of the central frequency $f_0$ with a difference $\Delta f$, define the point in time of the next change in the central frequency $f_0$ with first time interval t1, and define the point in time of the next change in the difference $\Delta f$ with second time interval t2, so as for the central processing unit to generate the control signal by values which vary continuously while the output driver is operating, wherein the values of the central frequency $f_0$, the difference $\Delta f$, the first time interval t1, and the second time interval t2 are generated by the central processing unit in accordance with operation of a dynamic parameter generating unit.

Another objective of the present invention is to speed up the operation of switch components such that upper and lower edges of the waveform of a signal thus outputted manifest features of rapid reaction and therefore reduce the excessive heat otherwise generated because of an increase in the power consumption incurred during the slow process of the shutdown of the switch components.

In order to achieve the above and other objectives, the output driver of the present invention comprises: a switch accelerating unit with an input end connected to the central processing unit to receive the control signal, wherein the switch accelerating unit comprises a capacitor and a resistor which are connected in parallel; and a switching unit connected to the switch accelerating unit, the power supply, and the electrode assembly to responsively determine whether the voltage source P received through operation of the control signal S is outputted to the switching operation of the electrode assembly, wherein relationship among central frequency $f_0$ of the control signal, capacitance C of the capacitor of the switch accelerating unit, and resistance R of the resistor satisfies an inequality of $(1/f_0)<5RC$. Therefore, the switch accelerating unit is characterized in that: when the control signal causes the switch accelerating unit to shut down, charges accumulated in advance while a capacitor is ON form a negative voltage at a control end of the switching unit, so as to speed up the shutdown of the switching unit and therefore greatly reduce excessive heat otherwise generated because of an increase in the power consumption during the slow process of the shutdown of the switch components (in the situation where no negative voltage is applied.)

In an embodiment of the present invention, the output driver is a forward driver or a full-bridge driver. In the case of the forward driver, a single switching unit directly drives a voltage transforming unit in a corresponding electrode assembly. In the case of the full-bridge driver, switching units of the output driver are in the number of four and are divided into two switch groups. The input ends of the switch groups are connected to the central processing unit so as to be controlled by the central processing unit to therefore perform the switching operation. The output ends of the switch groups are connected to a positive pole of a voltage transforming unit of the electrode assembly. The output ends of the other switch groups are connected to a negative pole of the voltage transforming unit. The switch groups each comprising: two said switching units being a first switching unit and a second switching unit, respectively, wherein an input end of the first switching unit is connected to the power supply, and an output end of the first switching unit is connected to an input end of the second switching unit and the voltage transforming unit, wherein an output end of the second switching unit is grounded; and a said switch accelerating unit connected to a control end of the second switching unit and to the central processing unit to receive a corresponding control signal for controlling the second switching unit.

In an embodiment of the present invention, the switch groups each comprise another switch accelerating unit connected to a control end of the first switching unit and to the central processing unit to receive a corresponding control signal for controlling the first switching unit, and each said switching unit comprises a transistor and is parallel-connected between a stabilizing diode and a stabilizing capacitor between a collector and an emitter of the transistor, wherein a transistor of the first switching unit is a p-type semiconductor, and a transistor of the second switching unit is a n-type semiconductor.

Yet another objective of the present invention is to allow an electrotherapy device to perform fine adjustment of voltage.

In order to achieve the above and other objectives, the power supply of the present invention comprises a power generator and an output value leader (OVL). The power generator outputs a rated voltage to the output value leader for undergoing modulation. The output value leader comprises: a first-stage adjusting unit for receiving the rated voltage such that a built-in variable resistor provides first-stage voltage adjustment and generates an output; and a plurality of second-stage adjusting units connected to the first-stage adjusting unit to receive its output, such that a built-in variable resistor provides second-stage voltage adjustment and sends an output to a corresponding output driver. Therefore, since the resistance control is carried out at the power supply of the electrotherapy device in two stages, knob-based (for adjusting a variable resistor) operation and control of the electrotherapy device achieves precise voltage control to therefore allow the spectral electrotherapy device of the present invention to provide users with precise output voltage.

A further objective of the present invention is to further reduce the sources of heat generated.

In order to achieve the above and other objectives, in the output driver of the present invention, the switching unit is a transistor, and there is no resistor between the collector and the base of the transistor, wherein the transistor is a circuit switch component. Therefore, in an output driver of the spectral electrotherapy device of the present invention, each switch simply functions as a circuit switch component instead of a variable resistor, which has resistance inversely proportional to the collector current of the transistor, because the spectral electrotherapy device of the present invention is not series-connected to a load through features of a transistor as a conventional electrotherapy device is. Hence, the spectral electrotherapy device of the present invention further prevents the switches from generating heat arising from excessive high power consumption.

BRIEF DESCRIPTION OF THE DRAWINGS

Objectives, features, and advantages of the present invention are hereunder illustrated with specific embodiments in conjunction with the accompanying drawings, in which.

DETAILED DESCRIPTION OF THE PREFERRED EMBODIMENTS

Figure 1:
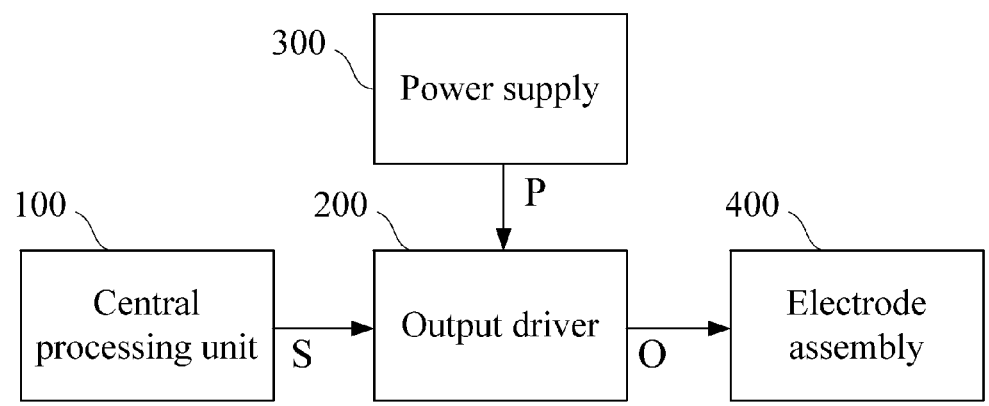
FIG. 1 is a function block diagram of a spectral electrotherapy device in an embodiment of the present invention.

Referring to FIG. 1, there is shown a function block diagram of a spectral electrotherapy device in an embodiment of the present invention. The spectral electrotherapy device of the present invention comprises a central processing unit 100, an output driver 200, a power supply 300, and an electrode assembly 400.

Since the central processing unit 100 provides a control signal S to the switching units in the output driver 200, a voltage source P provided by the power supply 300 connected to the output driver 200 generates an output voltage O through the switching operation of the output driver 200. The output voltage O is sent to the electrode assembly 400 connected to the output driver 200 so as to form an output with a frequency which changes continuously. The electrode assembly 400 has electrodes which are attached to the user's skin so that the output attains electrotherapeutic efficacy for the user.

The spectral electrotherapy device of the present invention is characterized in that the central processing unit controls the control signal S to operate the output driver 200 accordingly. The control signal S uses a central frequency $f_0$ as a standard, defines the bandwidth of the central frequency $f_0$ with a difference $\Delta f$, defines the point in time of the next change in the central frequency $f_0$ with first time interval t1, and defines the point in time of the next change in the difference $\Delta f$ with second time interval t2. The first time interval t1 and the second time interval t2 define the position of the range of frequencies of the control signal S and the point in time of a change in bandwidth. When they are ever-changing, the first time interval t1 and the second time interval t2 together complicate the changes in the control signal S and therefore are insusceptible to the human body's self-adaptation. The central processing unit 100 generates the control signal S through a dynamic parameter generating unit (not shown) for generating ever-changing $f_0$, $\Delta f$, t1, and t2 while the output driver 200 is operating. For example, the dynamic parameter generating unit stores multiple computation functions in the central processing unit 100 or are stored in another storage to provide the functions to the central processing unit 100 for performing computation to generate the control signal S. The values of $f_0$, $\Delta f$, t1, and t2 provide continuous changes in a parameter in accordance with their respective functions; for example, when accessed with different matrices, each function generates an ever-changing parameter. For example, a function is substituted into 1~50 independent variable matrices in sequence (to form a "continuous" parameter), then into 50~1 independent variable matrices in sequence, and eventually into the other independent variable matrices. For example, the function is substituted into 1~30 independent variable matrices in sequence and then into 30~1 independent variable matrices in sequence, wherein the quantity of data of the function to be substituted into each matrix depends on the difference between t1 and t2 In short, in doing so, it is feasible to generate a continuous output of ever-changing complete energy, such that acupuncture points, lesions, or trigger points which lie in the human body's tissues and have different depths can be fully stimulated, and in consequence the regularity of the control signal S is unlikely to be memorized by the human body. In a preferred embodiment, the control signal S is controlled in a manner that it does not manifest repetitious regularity within at least a preset time (such as 10 minutes).

In an embodiment, take medium-frequency electrotherapy as an example, the spectral electrotherapy device of the present invention operates at 1 k~100 kHz such that the control signal S defined jointly with the central frequency $f_0$ and the difference $\Delta f$ is controlled by the central processing unit 100 to oscillate at a specific range of frequencies.

Figure 2A:
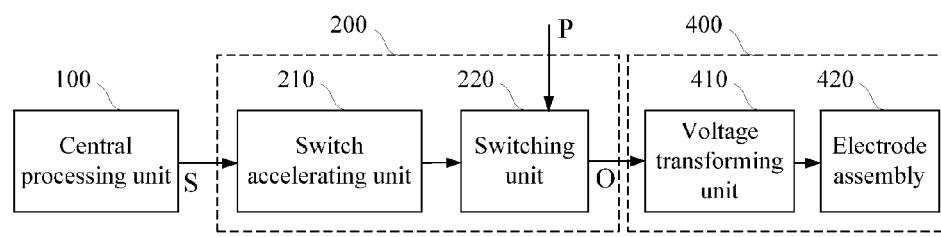
FIG. 2A is a schematic view of the circuit layout of an output driver and an electrode assembly in an embodiment of the present invention.

Referring to FIG. 2A, there is shown a schematic view of the circuit layout of an output driver and an electrode assembly in an embodiment of the present invention. In this embodiment, the output driver 200 comprises a switch accelerating unit 210 and a switching unit 220.

An input end of the switch accelerating unit 210 is connected to the central processing unit 100 to receive the control signal S. The switch accelerating unit 210 comprises a capacitor and a resistor which are connected in parallel. The switching unit 220 is connected to the switch accelerating unit 210, the power supply 300, and the electrode assembly 400 to responsively determine whether the voltage source P received through the operation of the control signal S is outputted to the switching operation of the electrode assembly 400.

The present invention is uniquely configured as follows: the relationship among central frequency f0 of the control signal S, capacitance C of the capacitor of the switch accelerating unit 210, and resistance R of the resistor satisfies the inequality $(1/f0) < 5RC$. Once the inequality is satisfied, the capacitor and the resistor which are connected in parallel can greatly reduce the OFF time (the speed of the descent of the lower edge of the signal) required by the switching unit 220 because, given the aforesaid configuration of the present invention, the capacitor applies a negative voltage to the switching unit 220 when the control signal S effectuates low-voltage OFF control to thereby provide a reverse-bias voltage and allows the switching unit 220 to produce a voltage-boosting shut-off effect.

Figure 2B:
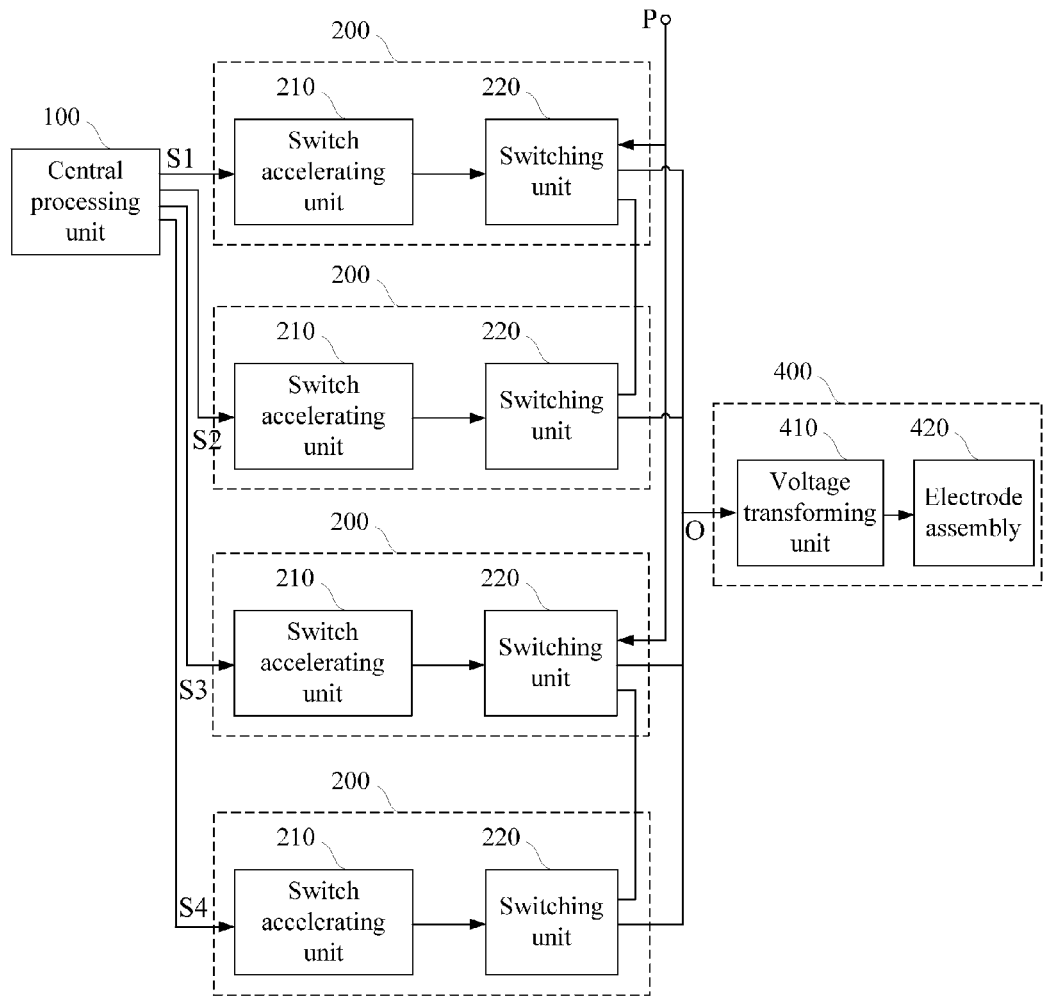
FIG. 2B is a schematic view of the circuit layout of the output driver and the electrode assembly in another embodiment of the present invention.

Referring to FIG. 2B, there is shown a schematic view of the circuit layout of the output driver and the electrode assembly in another embodiment of the present invention. The spectral electrotherapy device of the present invention generates the output of multiple channels. The channels each comprise different amounts of output drivers 200, depending on circuit design. FIG. 2A shows a forward driver circuit, wherein the output of a single channel is achieved by a single output driver 200. FIG. 2B shows a full-bridge driver circuit with a channel which comprises four output drivers 200. Furthermore, since each output driver 200 comprises a switching unit, each output driver 200 is controlled with control signals S1~S4 provided by the central processing unit 100 (illustrated with FIG. 2B), and each channel uses an output of the power supply 300.

Figure 3A:
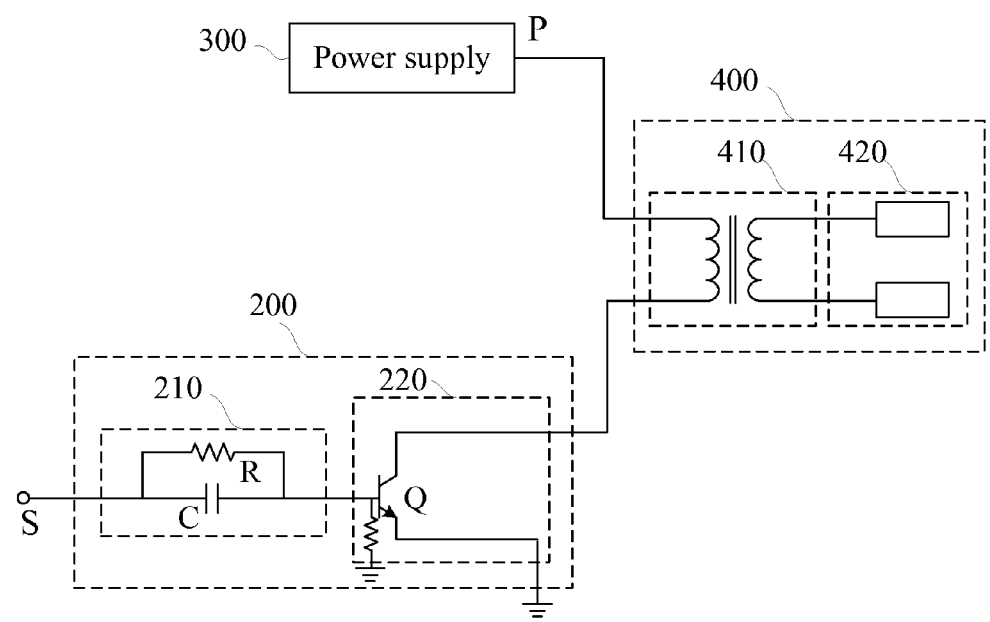
FIG. 3A is a schematic view of the circuit layout of the spectral electrotherapy device with a forward driver circuit in an embodiment of the present invention.

Referring to FIG. 3A, there is shown a schematic view of the circuit layout of the spectral electrotherapy device with a forward driver circuit in an embodiment of the present invention. The switching unit 220 has one end grounded and has the other end connected to the electrode assembly 400. The other end of the electrode assembly 400 is connected to the output of the power supply 300. Hence, when the switching unit 220 is ON (for example, when the control signal S is at a high level), it can be grounded, and the output of the power supply 300 is provided to the electrode assembly 400 through a loop thus formed. Conversely, when the switching unit 220 is OFF (for example, when the control signal S is at a low level), the loop thus formed breaks, and the output of the power supply 300 cannot be provided to the electrode assembly 400, thereby generating an output voltage.

Figure 3B:
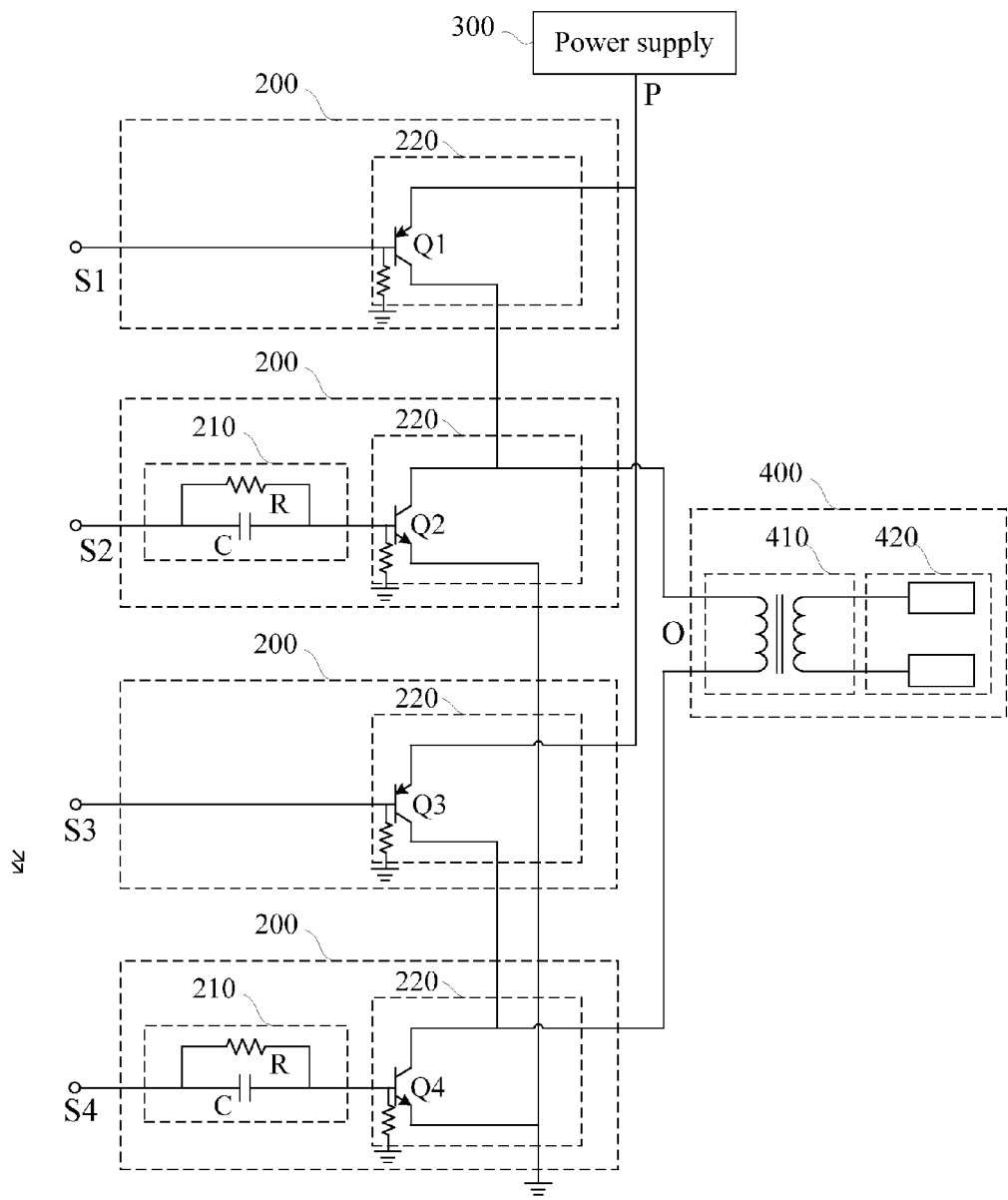
FIG. 3B is a schematic view of the circuit layout of the spectral electrotherapy device with a full-bridge driver circuit in an embodiment of the present invention.

Referring to FIG. 3B, there is shown a schematic view of the circuit layout of the spectral electrotherapy device with a full-bridge driver circuit in an embodiment of the present invention. The switching units 220 of the output driver 300 are in the number of four and are divided into two switch groups. The input ends of the switch groups are connected to the central processing unit 100 so as to be controlled by the central processing unit 100 to therefore perform the switching operation. The output ends of switch groups Q1, Q2 are connected to a positive pole of a voltage transforming unit 410 of the electrode assembly 400. The output ends of another switch groups Q3, Q4 are connected to a negative pole of the voltage transforming unit 410. The switch groups each comprise switch groups Q1 and Q2, Q3 and Q4 of the two switching units 220 and one said switch accelerating unit 210. The two switching units 220 are first switching units Q1, Q3 and second switching units Q2, Q4, respectively. The input ends of the first switching units Q1, Q3 are connected to the power supply 300. The output ends of the first switching units Q1, Q3 are connected to the input ends of the second switching units Q2, Q4 and the voltage transforming unit 410. The output ends of the second switching units Q2, Q4 are grounded. The switch accelerating unit 210 is connected to a control end of the second switching units Q2, Q4. The switch accelerating unit 210 is connected to the central processing unit 100 to receive corresponding control signals S2, S4 for controlling the second switching units Q2, Q4.

Figure 3C:
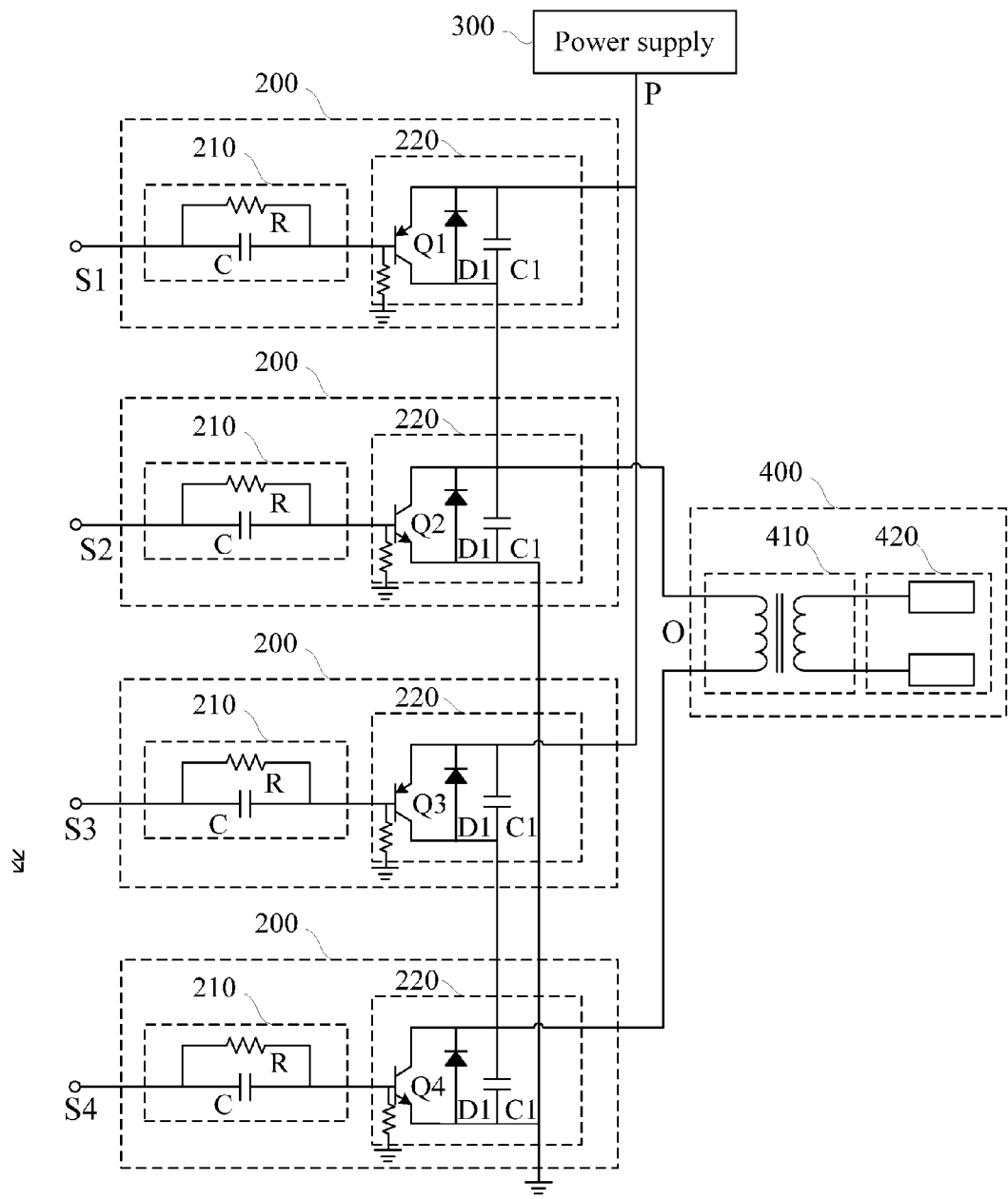
FIG. 3C is a schematic view of the circuit layout of the spectral electrotherapy device with a full-bridge driver circuit in another embodiment of the present invention.

Referring to FIG. 3C, there is shown a schematic view of the circuit layout of the spectral electrotherapy device with a full-bridge driver circuit in another embodiment of the present invention. The diagram shows additional technical features of the two portions in this embodiment. A technical feature of the present invention is that the switch groups Q1 and Q2, Q3 and Q4 each further comprise another said switch accelerating unit 210 connected to a control end of the first switching units Q1, Q3 and connected to the central processing unit 100 to receive corresponding control signal for controlling the first switching units Q1, Q3. Another technical feature of the present invention is that the switching units each comprise transistors Q1 and Q2, Q3 and Q4 and a stabilizing diode D1 and a stabilizing capacitor C1 which are parallel-connected between a collector and an emitter of the transistor, wherein the transistor of the first switching units Q1, Q3 is a p-type semiconductor, and the transistor of the second switching units Q2, Q4 is a n-type semiconductor. Therefore, the parallel-connected stabilizing diode D1 limits the voltage between the collector and the emitter of transistors Q1~Q4 to 0.6V~input power voltage +0.6V. When the primary coil of the voltage transforming unit 410 generates a counter-electromotive force in response to a change in the input voltage, the stabilizing diode D1 provides the counter-electromotive force bypass for preventing transistors Q1~Q4 from getting damaged. The parallel-connected stabilizing capacitor C1 reduces the noise otherwise arising from the switching of the stabilizing diode D1 and the transistors Q1~Q4 and has a low capacitive impedance to therefore allow high-frequency noise to enter the stabilizing capacitor C1 functioning as a bypass and prevent the transistors Q1~Q4 from being heated up because of the high-frequency noise.

Figure 4:
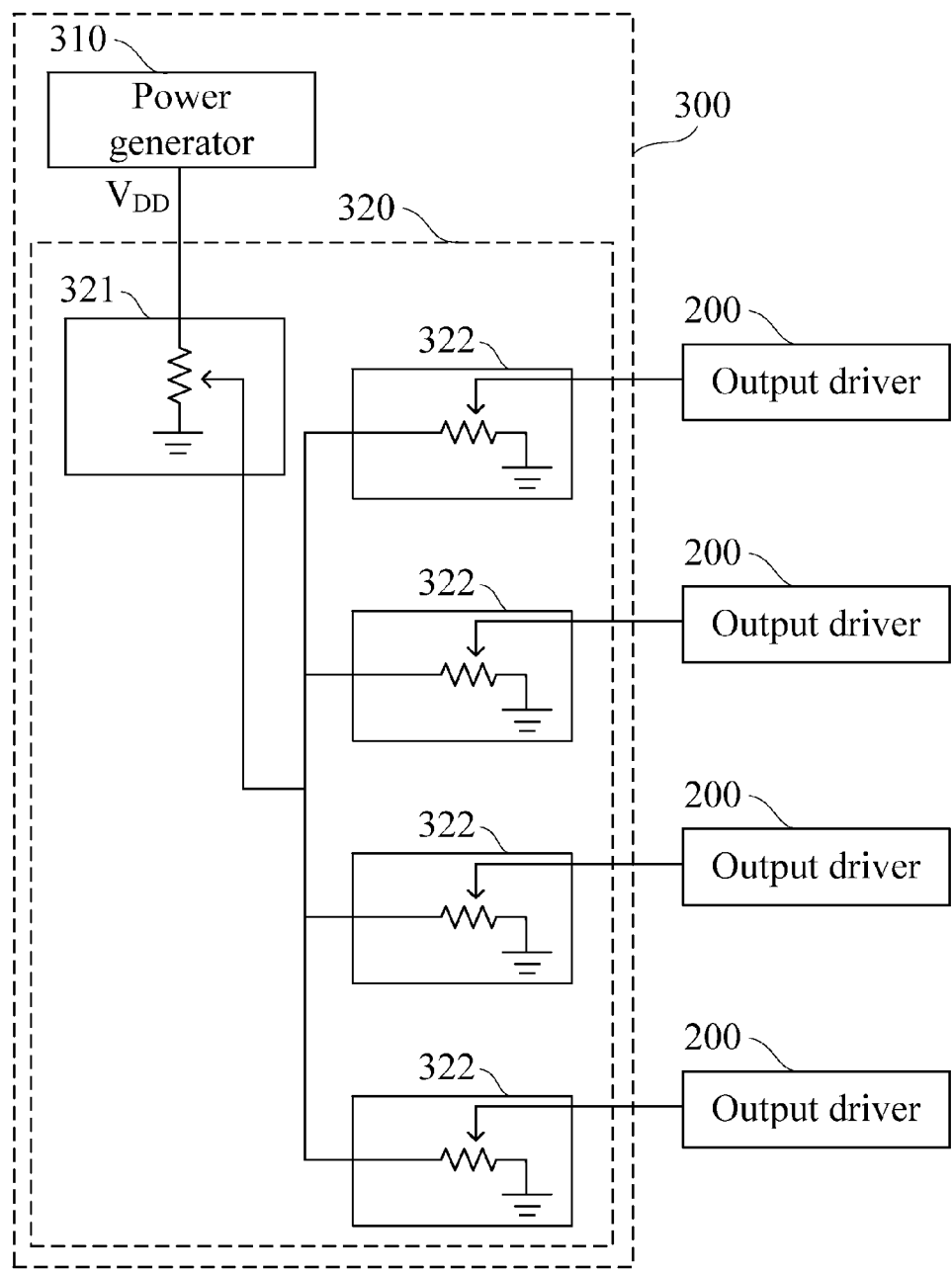
FIG. 4 is a schematic view of the circuit layout of a power supply with an output value leader (OVL) in yet another embodiment of the present invention.

Referring to FIG. 4, there is shown a schematic view of the circuit layout of a power supply with an output value leader (OVL) in yet another embodiment of the present invention. The power supply 300 comprises a power generator 310 and an output value leader 320. The power generator 310 outputs a rated voltage $V_{DD}$ (such as 5V) to the output value leader 320 for undergoing modulation. The output value leader 320 comprises a first-stage adjusting unit 321 and a plurality of second-stage adjusting units 322. The first-stage adjusting unit 321 not only receives the rated voltage $V_{DD}$ but also uses a built-in variable resistor to provide first-stage voltage adjustment and generate an output. The second-stage adjusting units 322 are connected to the first-stage adjusting unit 321 to receive its output. The second-stage adjusting units 322 use a built-in variable resistor to provide second-stage voltage adjustment and send an output to the corresponding output driver 200.

Figure 5:
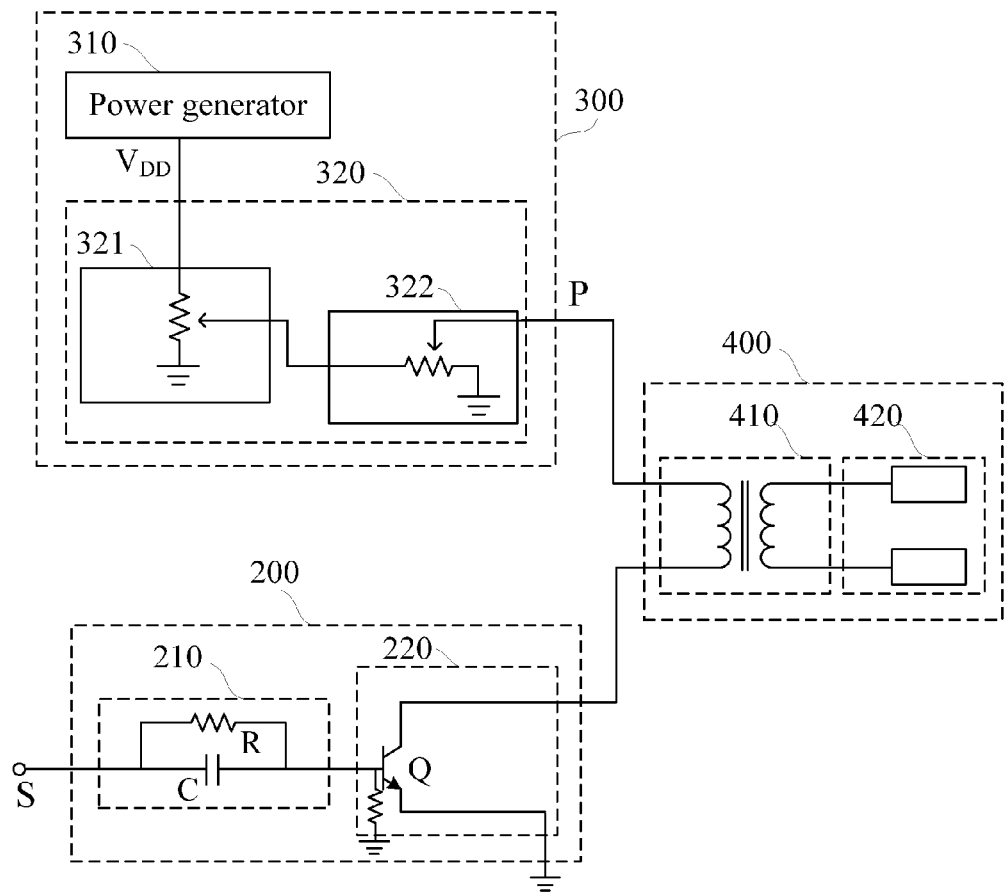
FIG. 5 is a schematic view of the circuit layout of the output driver in a further embodiment of the present invention.

Referring to FIG. 5, there is shown a schematic view of a circuit layout of an output driver in a further embodiment of the present invention. As shown in FIG. 5, there is no resistor between the collector and the base of the transistor of the switching unit 220. The transistor is a circuit switch component. Each switch simply functions as a circuit switch component instead of a variable resistor, which has resistance inversely proportional to the collector current of the transistor, because the spectral electrotherapy device of the present invention is not series-connected to a load through features of a transistor as a conventional electrotherapy device is. Hence, the spectral electrotherapy device of the present invention further prevents the switches from generating heat arising from excessive high power consumption.

The present invention is disclosed above by preferred embodiments. However, persons skilled in the art should understand that the preferred embodiments are illustrative of the present invention only, but should not be interpreted as restrictive of the scope of the present invention. Hence, all equivalent changes and replacements made to the aforesaid embodiments should fall into the scope of the present invention. Accordingly, protection for the present invention should be defined by the appended claims.

What is claimed is:

1. A spectral electrotherapy device, having a central processing unit for providing a control signal to a switching unit of an output driver such that a voltage source provided by a power supply connected to the output driver generates an output voltage through a switching operation performed by the output driver, wherein the output voltage is sent to an electrode assembly connected to the output driver to thereby generate an output of the spectral electrotherapy device, characterized in that:

the central processing unit uses a central frequency $f_0$ as a standard for the control signal provided by the corresponding switching unit to define a bandwidth of the central frequency $f_0$ with a difference $\Delta f$, define a point in time of a next change in the central frequency $f_0$ with a first time interval t1, and define a point in time of a next change in the difference $\Delta f$ with a second time interval t2, wherein values of the central frequency $f_0$, the difference $\Delta f$, the first time interval t1, and the second time interval t2 change continuously while the output driver is operating so as to enable the central processing unit to generate the control signal in accordance with the operation of a dynamic parameter generating unit.

2. The spectral electrotherapy device of claim 1, wherein the control signal defined jointly with the central frequency $f_0$ and the difference $\Delta f$ is controlled by the central processing unit to oscillate at 1k~100 kHz.

3. The spectral electrotherapy device of claim 1, wherein the output driver comprises:

a switch accelerating unit with an input end connected to the central processing unit to receive the control signal, wherein the switch accelerating unit comprises a capacitor and a resistor which are connected in parallel; and a switching unit connected to the switch accelerating unit, the power supply, and the electrode assembly to responsively determine whether the voltage source P received through operation of the control signal S is outputted to the switching operation of the electrode assembly, wherein relationship among central frequency $f_0$ of the control signal, capacitance C of the capacitor of the switch accelerating unit, and resistance R of the resistor satisfies an inequality of $(1/f_0)<5RC$.

4. The spectral electrotherapy device of claim 3, wherein the output driver is a forward driver, and the switching unit drives a voltage transforming unit in a corresponding electrode assembly.

5. The spectral electrotherapy device of claim 4, wherein the switching unit is a transistor, and no resistor is disposed between a collector and a base of the transistor, wherein the transistor is a circuit switch component.

6. The spectral electrotherapy device of claim 5, wherein the power supply comprises a power generator and an output value leader, wherein the power generator outputs a rated voltage to the output value leader for undergoing modulation, wherein the output value leader comprises:

a first-stage adjusting unit for receiving the rated voltage so as for a built-in variable resistor to provide first-stage voltage adjustment and generate an output; and a plurality of second-stage adjusting units connected to the first-stage adjusting unit to receive its output so as for a built-in variable resistor to provide second-stage voltage adjustment and send an output to the corresponding output driver.

7. The spectral electrotherapy device of claim 3, wherein the output driver is a full -bridge driver, wherein the switching unit of the output driver is in number of four and is divided into two switch groups, wherein input ends of the switch groups are connected to the central processing unit so as to be controlled by the central processing unit to therefore perform the switching operation, wherein output ends of the switch groups are connected to a positive pole of a voltage transforming unit of the electrode assembly, wherein output ends of the other switch groups are connected to a negative pole of the voltage transforming unit, the switch groups each comprising:

two said switching units being a first switching unit and a second switching unit, respectively, wherein an input end of the first switching unit is connected to the power supply, and an output end of the first switching unit is connected to an input end of the second switching unit and the voltage transforming unit, wherein an output end of the second switching unit is grounded; and a said switch accelerating unit connected to a control end of the second switching unit and to the central processing unit to receive a corresponding control signal for controlling the second switching unit.

8. The spectral electrotherapy device of claim 7, wherein the switch groups each further comprise another said switch accelerating unit connected to a control end of the first switching unit and to the central processing unit to receive the corresponding control signal for controlling the first switching unit.

9. The spectral electrotherapy device of claim 8, wherein each said switching unit comprises a transistor and is parallel-connected between a stabilizing diode and a stabilizing capacitor between a collector and an emitter of the transistor, wherein a transistor of the first switching unit is a p-type semiconductor, and a transistor of the second switching unit is a n-type semiconductor.

10. The spectral electrotherapy device of claim 9, wherein no resistor is disposed between a collector and a base of the transistor, and the transistor is a circuit switch component.

11. The spectral electrotherapy device of claim 3, wherein the power supply comprises a power generator and an output value leader, wherein the power generator outputs a rated voltage to the output value leader for undergoing modulation, wherein the output value leader comprises:
- a first-stage adjusting unit for receiving the rated voltage so as for a built-in variable resistor to provide first-stage voltage adjustment and generate an output; and
- a plurality of second-stage adjusting units connected to the first-stage adjusting unit to receive its output so as for a built-in variable resistor to provide second-stage voltage adjustment and send an output to a corresponding one of the output drivers.

12. A method of controlling a spectral electrotherapy device, wherein the spectral electrotherapy device provides a control signal to a switching unit of an output driver through a central processing unit, such that a voltage source provided by a power supply connected to the output driver generates an output voltage through the switching operation of the output driver, wherein the output voltage is sent to an electrode assembly connected to the output driver for generating an output of the spectral electrotherapy device, the method is characterized in that:
- the control signal uses a central frequency $f_0$ as the standard to thereby define the bandwidth of the central frequency $f_0$ with a difference $\Delta f$, define the point in time of the next change in the central frequency $f_0$ with a first time interval t1, and define the point in time of the next change in the difference $\Delta f$ with a second time interval t2, so as to enable the central processing unit to generate the control signal by values which vary continuously while the output driver is operating,
- wherein the values of the central frequency $f_0$, the difference $\Delta f$, the first time interval t1, and the second time interval t2 are generated by the central processing unit in accordance with operation of a dynamic parameter generating unit.

* * * * *